US010962476B2

(12) United States Patent
Riding et al.

(10) Patent No.: US 10,962,476 B2
(45) Date of Patent: Mar. 30, 2021

(54) TURBIDITY SENSOR AND METHOD FOR MEASURING TURBIDITY (71) Applicant: Process Instruments (UK) LTD, Burnley (GB)

(72) Inventors: Mike Riding, Burnley (GB); Craig Stracey, Burnley (GB)

(73) Assignee: Process Instruments (UK) Ltd., Burnley (GB)

( * ) Notice: Subject to any disclaimer, the term of this patent is extended or adjusted under 35 U.S.C. 154(b) by 278 days.

(21) Appl. No.: 16/315,131

(22) PCT Filed: Jun. 23, 2017

(86) PCT No.: PCT/GB2017/051838
§ 371 (c)(1),
(2) Date: Jan. 3, 2019

(87) PCT Pub. No.: WO2018/007786
PCT Pub. Date: Jan. 11, 2018

(65) Prior Publication Data
US 2019/0234873 A1    Aug. 1, 2019

(30) Foreign Application Priority Data
Jul. 4, 2016  (GB) ..................... 1611650

(51) Int. Cl.
*G01N 21/53*     (2006.01)
*G01N 15/06*     (2006.01)
(Continued)

(52) U.S. Cl.
CPC ............. *G01N 21/53* (2013.01); *G01N 15/06* (2013.01); *G01N 21/276* (2013.01);
(Continued)

(58) Field of Classification Search
CPC ........... G01N 21/4785; G01N 21/8507; G01N 2021/4726; G01N 15/06;
(Continued)

(56) References Cited

U.S. PATENT DOCUMENTS

2005/0264817 A1  12/2005  Havard et al.
2010/0225920 A1   9/2010  Xia et al.
2011/0273705 A1  11/2011  Rao et al.

FOREIGN PATENT DOCUMENTS

DE    10 2009 002 145 B3    11/2010
EP              1228358 A1     8/2002
(Continued)

OTHER PUBLICATIONS

Written Opinion and International Search Report of the International Searching Authority, International application No. PCT/GB2017/051838, dated Sep. 12, 2017. European Patent Office, Rijswijk, NL.

(Continued)

*Primary Examiner* — Hina F Ayub
*Assistant Examiner* — Amanda Merlino
(74) *Attorney, Agent, or Firm* — Gregory Finch; Finch Paolino, LLC (57) ABSTRACT Sensor and Measurement Method A turbidity sensor and method of measuring turbidity is provided. The turbidity sensor (100) comprises first and second optical detectors for detecting a respective optical response of each optical signal. The first optical detector (20) may be arranged in direct view of the emitter (10) and the second optical detector (30) may be arranged in indirect view of the emitter (10). The two detectors collect light emitted from the emitter (10) when directed through a fluid sample during two optical tests run in very close succession. Firstly, a control sample is illuminated to determine a calibration factor for the control sample (Continued)

with known turbidity. Then, the calibration factor is used to determine the turbidity of a fluid sample with unknown turbidity. Advantageously, background radiation during the data collection process is ignored because the transient behaviour during each optical test is negligible. The approach is more convenient over known turbidity sensors and measurement methods, particularly in light of the calibration step.

18 Claims, 5 Drawing Sheets

(51) Int. Cl.
    *G01N 21/27*      (2006.01)
    *G01N 33/18*      (2006.01)
    *G01N 21/47*      (2006.01)
    *G01N 21/85*      (2006.01)
    *G01N 15/00*      (2006.01)

(52) U.S. Cl.
    CPC ......... *G01N 21/4785* (2013.01); *G01N 33/18* (2013.01); *G01N 21/8507* (2013.01); *G01N 2015/0053* (2013.01); *G01N 2015/0693* (2013.01); *G01N 2021/4726* (2013.01); *G01N 2201/062* (2013.01); *G01N 2201/0633* (2013.01); *G01N 2201/12746* (2013.01)

(58) Field of Classification Search
    CPC ... G01N 2015/0053; G01N 2015/0693; G01N 21/276; G01N 21/53; G01N 2201/062; G01N 2201/0633; G01N 2201/12746; G01N 33/18; G01N 21/49
    See application file for complete search history.

(56) References Cited

FOREIGN PATENT DOCUMENTS

| | | |
|---|---|---|
| GB | 2355524 A | 4/2001 |
| WO | 9623208 A1 | 8/1996 |
| WO | 0129541 A1 | 4/2001 |
| WO | 2010059176 A1 | 5/2010 |
| WO | 2012134820 A1 | 10/2012 |

OTHER PUBLICATIONS

Search Report, application No. GB1611650.1, dated Dec. 8, 2016. UK Intellectual Property Office, Newport, South Wales, UK.

TURBIDITY SENSOR AND METHOD FOR MEASURING TURBIDITY

FIELD

The disclosure relates to a turbidity sensor and method of measuring turbidity.

BACKGROUND

Turbidity is commonly used as a measure of water quality and gives an indication of how clean water is. It is commonly measured by illuminating a sample with a light source and measuring the response through the sample by a turbidity sensor. The turbidity sensor measures the amount of light scatter in the sample by the particles within the sample. Although a high particle concentration generally results in a high scattered signal, high particle concentrations can also give lower scattered signals once absorption becomes dominant and the light is attenuated.

When a turbidity measurement is made, the signal produced by the detector is composed of two components; the signal due to the scattered light through the sample and the signal due to the background light. Therefore, traditionally any background light must be subtracted from the total measured signal in order to isolate the actual output from the light source. When measurements are conducted in an uncontrolled environment, the background radiation will vary over time which means that traditionally the background radiation must be subtracted each time a measurement is taken. This is time consuming and laborious. Variations in background light will cause the result of the measurement to change, thus changing the apparent turbidity of a sample. At low levels, the background light can form a significant part of the total measured signal. The effect of background variation becomes even more significant if there is a difference between the background light when a calibration is made to when the measurement is made. The need to account for background radiation is inconvenient and is one of the reasons that makes calibration of instruments for turbidity measurements difficult. Furthermore, many calibration procedures require a measurement to be made with a calibration sample that is as close to 0 NTU (nephelometric turbidity unit, the unit of measurement of turbidity) as possible (pure water is around 0.018 NTU). However, such a sample is difficult to obtain and the measurement of such a sample will still be significantly affected by the background light levels.

It is therefore desirable to provide a turbidity sensor and method of measuring turbidity that removes the need to account for background radiation. Therefore an alternative solution to accurately collecting turbidity measurements is desired. A more convenient solution that provides a high level of performance is advantageous in order to achieve an accurate and fast acquisition of data collection. Ultimately, the aim is to provide a better turbidity sensor and method that is more user-friendly in order to overcome the disadvantages and drawbacks associated with conventional turbidity sensors.

SUMMARY

According to the present invention there is provided a turbidity sensor and method of measuring turbidity as set forth in the appended claims. Other features of the invention will be apparent from the dependent claims, and the description which follows.

According to the disclosure, a method of measuring turbidity is provided. The method includes conducting an optical test on a control fluid with known turbidity and repeating the optical test on a sample fluid with unknown turbidity. Each time, the optical test may be run under the same conditions or different conditions. For example, the optical test points for the control fluid be the same or different to the optical test points for the sample fluid. The optical test comprises the emission of a plurality of optical signals from an emitter toward the fluid. The emitter may be a light source such as an LED (light emitting diode) or a plurality of LEDs (i.e. an array of LEDs). The optical signal may be a collimated optical signal, which is collimated by a collimating tube. Each optical signal has a different optical setting amongst a particular optical characteristic. For example, the optical characteristic may be light intensity and the optical setting may be a particular light intensity. For each optical signal a reference signal and a fluid signal is captured. The reference signal is captured by detecting an optical response of the optical signal received by a first optical detector before the optical signal has entered the fluid. Therefore, the first optical detector and emitter may be sealed from the fluid by a fluid barrier. The fluid barrier may be a window, such as a sapphire window. The first optical detector may be in the optical path of the emitter. Preferably, the first optical detector is in direct view of the emitter. That is, said first optical detector may be in line of sight of the emitter. Alternatively, the first optical detector may receive an indirect optical signal. That is, the optical signal may be reflected from the fluid barrier (i.e. a sapphire window). The fluid barrier may be positioned at an outlet of a collimating tube, wherein the emitter is interposed between the tube outlet the first optical detector. The fluid signal is captured by detecting an optical response of the optical signal received by a second optical detector in indirect view of the emitter. That is, said second optical detector may not be in line of sight of the emitter. Once the reference and fluid signals have been captured, the method includes determining a calibration factor of the turbidity sensor. By repeating the optical test for the sample fluid and collecting the reference and fluid signals from the sample fluid at a plurality of optical signals that may be different from the control fluid test, the turbidity of the sample fluid is determined based on the calibration factor. Advantageously, an alternative data collection process is provided. When the optical signals are carried out in close succession (i.e. at a frequency of at least 1 Hz), the influence of background radiation is negligible. Furthermore, the reference signal also helps to reduce problems associated with temperature effects in optical measurements. This is because particular optical signals, such as visible light signals, vary with temperature and such changes will be accounted for in both the reference and fluid signals.

The calibration factor may be determined by plotting a regression line of the reference and fluid signals captured for the control fluid and dividing the known turbidity of the control fluid by the gradient of the regression line. That is, the reciprocal of the gradient of a calibration regression line plotted between the reference and fluid signals captured for the control fluid is multiplied by the known turbidity. The turbidity of the sample fluid may be determined by plotting a regression line of the reference and fluid signals captured for the sample fluid and multiplying the calibration factor by the gradient of the regression line.

Preferably, the turbidity sensor comprises a controller for controlling the emitter. The controller may be further arranged for controlling the first and second optical detectors. The controller may control the frequency of optical signals during an optical test. The controller may comprise a memory for storing detected signals, such as a plurality of reference and fluid signals and/or other information related to the turbidity measurements, such as a calibration factor and/or the turbidity of a sample fluid. The controller may be arranged for calculating the known turbidity of a sample fluid.

Preferably, the first and second optical detectors are photodetectors such as photodiodes. Preferably, the optical test is repeated on a plurality of sample fluids without needing to update the calibration factor. That is, the method may comprise repeating the optical test a plurality of times, wherein each time the optical test is run on a different sample fluid with unknown turbidity. Advantageously, a single control fluid can be used to measure the turbidity of a plurality of fluid samples.

Preferably, a primary optical signal is composed as part of the plurality of optical signals. That is, one of the plurality of optical signals is a primary optical signal. The remaining optical signals are non-primary optical signals. The optical setting of each non-primary optical signal may be substantially 10% to 90% of the optical setting of the primary optical signal. Alternatively, the optical setting of each non-primary optical signal may be substantially 25% to 75% of the optical setting of the primary optical signal.

Preferably, the optical characteristic is light intensity (i.e. luminance). The light intensity may otherwise be called brightness and may be determined by the power of the emitter. The optical setting of the primary optical signal may be created at substantially full power of the emitter. The variation in light intensity may be achieved electronically or mechanically. For example, the current of the emitter may be varied or a shutter in front of the emitter may open or close to impede the amount of light that is emitted.

Preferably, the frequency of the plurality of optical signals for the optical test is at least 1 Hz. Alternatively, the frequency may be at least 5 Hz or at least 10 Hz. That is, the time interval between optical tests for each fluid (whether control or sample) may be up to 1 s, 0.2 s or 0.1 s. Preferably, the duration of the optical signal is around 100 ms to allow good noise rejection, particularly 50/60 Hz noise rejection and to give enough time for the emitter and detectors to respond. A waiting time between the end of an optical signal and the start of the proceeding optical signal may be around 10 ms. The optical setting (i.e. the output intensity) may be changed during the waiting time. That is, the time interval between optical tests for each fluid may be up to 0.11 s. Preferably, the time interval is between 0.01 s and 0.5 s. Most preferably, the time interval is between 0.05 and 0.2 s. Advantageously, the close succession of optical signals allows the effect of background radiation to be ignored because any changes in background are negligible. When the tests are carried out at substantially steady state or stationary background levels, the additional effect on the optical response is constant. Background radiation is any optical source that is not from the emitter, for example ambient light.

According to the disclosure, a turbidity sensor is provided. The turbidity sensor comprises housing having an emitter and first and second optical detectors coupled to the housing. The emitter is arranged to emit a plurality of optical signals so that each optical signal has a different optical setting that is derived from a particular optical characteristic. Each of the plurality of optical signals may be emitted sequentially and at different times. The emitter may be an LED or a plurality of LEDs. The optical signal may be a collimated optical signal. The first and second optical detectors are configured to detect a respective optical response of each optical signal. The arrangement of the first and second detectors is used to affect the optical response detected from the emitter. The first optical detector is arranged to receive the maximum optical response because the first optical detector is preferably positioned closer to the emitter than the second optical detector. Furthermore, the first optical detector is arranged to receive the optical signal before the optical signal has entered the fluid. Both the first and second optical detectors may be in indirect view of the emitter (i.e. not in line of sight). Alternatively, the first optical detector may be in direct view of the emitter (i.e. in line of sight), whereas the second optical detector may be arranged in indirect view of the emitter (i.e. not in line of sight). That is, the second optical detector may not in the direct beam path of the emitter. This allows the second optical detector to detect the influence of the fluid on the emitted optical signal whereas the first optical detector is not influenced by the optical scatter within the fluid. The first optical detector and emitter may be sealed from the fluid by a fluid barrier. The fluid barrier may be a window, such as a sapphire window. The fluid barrier may be positioned at an outlet of a collimating tube, wherein the emitter is interposed between the tube outlet the first optical detector.

Preferably, the turbidity sensor comprises a controller arranged to control the emitter. The controller may be further arranged to control the first and second optical detectors. The controller may control the frequency of optical signals during an optical test. The controller may comprise a memory to store detected signals, such as a plurality of reference and fluid signals and/or other information related to the turbidity measurements, such as a calibration factor and/or the turbidity of a sample fluid. The controller may be arranged to calculate the known turbidity of a sample fluid.

The turbidity sensor is a probe that emits and detects optical signals. The turbidity sensor may generally be an elongate member. One end of the turbidity sensor may comprise the two detectors and the emitter. The second optical detector may be located at a tip of the housing, which is a substantially distal location of the turbidity sensor.

The turbidity sensor may comprise a blocking member for blocking a direct line of incidence from the emitter to the second optical detector. The blocking member may be disposed between the first and second optical detectors. The housing may comprise a step (i.e. a stepped portion) which acts as the blocking member.

The first and second detectors may face in substantially the same direction as each other. The second detector may be arranged at substantially 90 degrees to a main line of incidence from the emitter. The second detector may be arranged anywhere between 90 degrees and 180 degrees to a main line of incidence from the emitter. Alternatively, the second detector may be arranged at substantially 135 degrees or 180 degrees (between 135 degrees and 180 degrees) to a main line of incidence from the emitter. That is, the angle between the direction that the first and second detectors face may be separated by an angle between 45 degrees or 90 degrees.

The turbidity sensor may comprise a collimating member for collimating the optical signal from the emitter. The collimating member may be a collimating tube. The housing may have a recess within which the collimating tube exists. The first optical detector and emitter may be located within the recess.

The turbidity sensor may be configured to be submersed in a liquid and prevent liquid ingress to electrical components. The turbidity sensor may therefore comprise sealing members for preventing the ingress of liquid beyond the emitter and the first and second optical detectors and into the housing when the turbidity sensor is submersed in liquid.

Beneficially, an alternative solution to accurately collecting turbidity measurements is provided. The turbidity sensor and method removes the effect of background noise to utilise a single calibration so that a plurality of turbidity measurements can be taken without needing to recalibrate the turbidity sensor. The alternative approach is more convenient whilst maintaining high accuracy. The disclosure herein is more convenient to a user and provides a better solution over conventional apparatuses and method.

BRIEF DESCRIPTION OF DRAWINGS

For a better understanding of the invention, and to show how embodiments of the same may be carried into effect, reference will now be made, by way of example, to the accompanying diagrammatic drawings in which.

DESCRIPTION OF EMBODIMENTS

Figure 1:
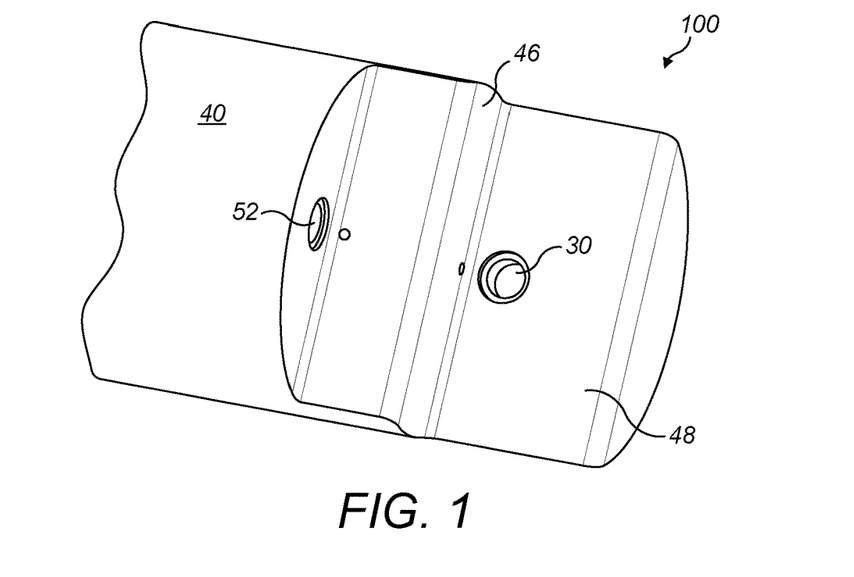
FIG. 1 shows a turbidity sensor of the present disclosure.
Figure 2:
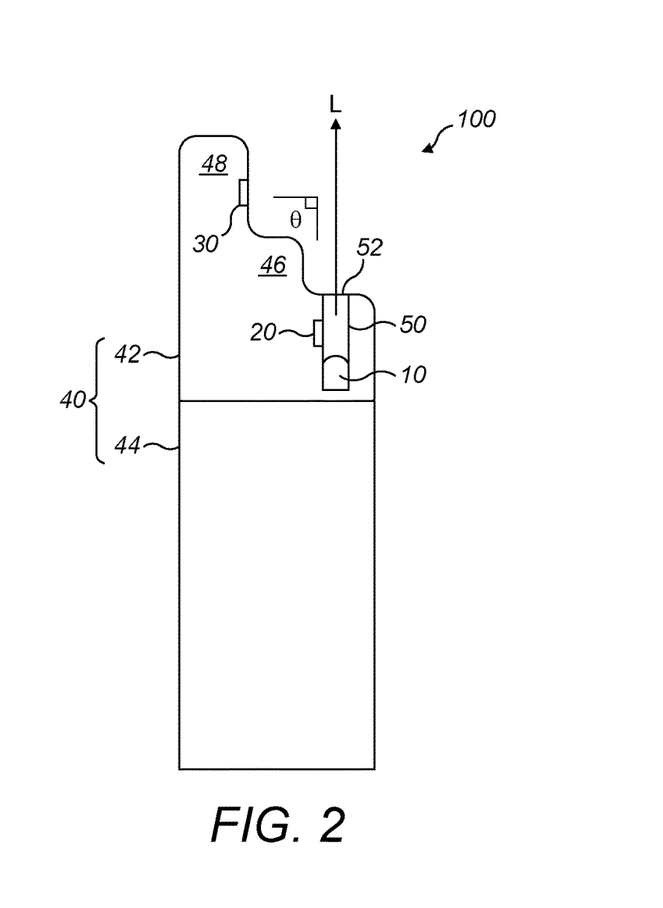
FIG. 2 shows a cross-sectional view of the turbidity sensor of FIG. 1.

FIGS. 1 and 2 show a turbidity sensor 100 comprising an emitter 10, a first optical detector 20 and a second optical detector 30 that are each coupled to a housing 40. The first optical detector 20 is located closer to the emitter 10 than the second optical detector 30 in order to measure the actual output of the emitter 10. The first optical detector 20 is shown in direct line of sight of the emitter 10 and is held within a hole in the wall of housing 40 by adhesive. In the example shown, the second optical detector 30 is positioned at a tip 48 of the housing 40 and at a relative angle θ of 90° (i.e. 90 degrees). That is, the relative angle θ is the angle between the central line of the detector and the main line of incidence L of the optical signal from the emitter 10. Once the optical signal from the emitter 10 has exited the housing 40, the optical signal enters a fluid and scatters within the fluid due to the fluid particles. The second optical detector 30 then detects the amount of scatter within the fluid. It is therefore important that the second optical detector 30 is not in the line of sight of the emitter 10 because the second optical detector 30 should not detect direct optical signals from the emitter 10. Conveniently, a blocking means, such as a stepped portion 46 is provided to prevent the direct signals being transferred from the emitter 10 to the second optical detector 30. However, the edge of an opening 52 to the emitter 10 may be used as the blocking means when the emitter is recessed into the housing 40. In the example shown, a plurality of blocking means is used to minimise the impact of incident optical signals from the emitter. The opening 52 may be a fluid barrier that prevents fluid entry. For example, the fluid barrier may be a sapphire window that allows an optical signal to pass but does not allow fluid to pass.

The emitter 10 is configured to emit light from the housing 40 by passing the light through a collimating member, such as a collimating tube 50. When a fluid barrier is used, the emitter 10 and first detector 20 may be on the 'dry' side, i.e. the side that does not contact the test fluid because the fluid cannot pass the fluid barrier. The light may be visible light or may be light that is invisible to the human eye, such as near-infrared light (i.e. light having a wavelength of around 850 nm to 860 nm). The light is then used to illuminate a fluid within which the turbidity sensor 100 is immersed (or at least the emitter 10 and detectors 20,30). The collimating tube 50 helps to collimate the emitted light from the housing 40 (e.g. align the optical signal in a parallel manner). Although the housing 40 shows the emitter 10 contained within the collimating tube 50, the emitter 40 and collimating tube 50 may both be contained within a recess within the housing 40. The second optical detector 20 may therefore receive optical signals from within the recess and/or the collimating tube 50.

In the example shown, the housing 40 is shown in two parts. The first part is a head 42 and the second is a base 44. The head 42 may be removable from the base 44 by so that the base 44 can be interchangeable with a variety of different heads. Each head 42 may comprise a different relative angle θ so that the second optical detector 30 may receive scattered signals at different positions. For example, relative angles θ of 135° or 180° may be used. The head 42 and base 44 may be coupled by the use of a fastening means such as a screw and thread. The fastening means may comprise a sealing member to prevent fluid ingress when the turbidity sensor is submersed in a fluid.

Figure 3:
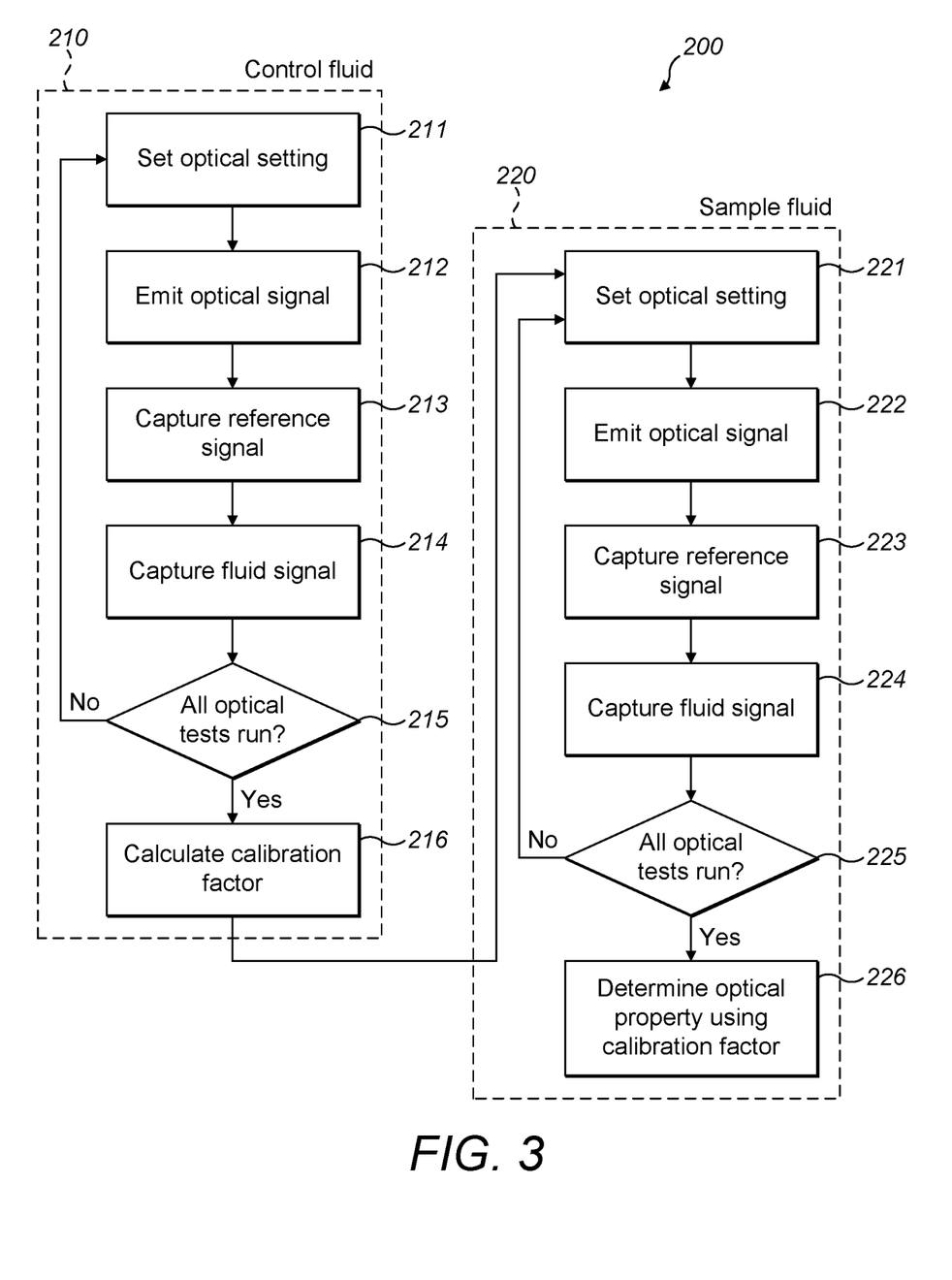
FIG. 3 shows a flow chart of the data collection process using the optical sensor of FIG. 1.

FIG. 3 shows a data collection method 200 using the optical sensor 100. The method 200 does not require the calculation of the background noise, such as background light, which means that calibrating the turbidity sensor 100 does not need to occur with every signal if a calibration factor has been calculated.

The method 200 starts by providing a control fluid (as shown in the left-hand box with dashed lines), which is used as a calibration sample. The turbidity sensor 100 is placed within the control fluid so that an optical test can be conducted 210. To start the first optical test 210, the optical setting of the turbidity sensor 100 is set 211. For example, the emitter 10 may be set to emit a light signal at full (i.e. 100%) power. Once the optical signal is emitted towards the fluid 212, the first 20 and second 30 detectors capture the optical response. Being in direct view (i.e. in the line of sight) of the emitter 10, the first optical detector 20 receives a strong signal from the emitter 10, which is considered to be the actual or reference optical signal. The reference signal is then captured 213 by the first detector 20. Simultaneously, a fluid signal is captured 214 by the second optical detector

30. Since the second optical detector 30 is not in direct view of the emitter 10 (i.e. in indirect view or out of the line of sight), this fluid signal is weaker than the reference signal. The detected optical signals are then recorded for later use to complete the first optical test.

Once the first optical test 210 is completed, a second optical test 210 is run. Preferably, the time between each optical test does not exceed 1s which allows a minimum frequency between optical tests of around 1 hz. Most preferably the maximum time is around 0.2 s (giving a frequency of around 5 Hz). A minimum of two optical tests must be run in order to calibrate the turbidity sensor 100 according to the control sample. The second optical test 210 is run at reduced power so that the emitter 10 sends an optical signal with lower intensity than the first optical test 210. For example, the light signal may be reduced to 75%, 50% or 25% power. Once again, the reference and fluid signals detected by the first 20 and second 30 optical detectors respectively are captured and recorded. The measured signals are then plotted against each other.

Figure 4:
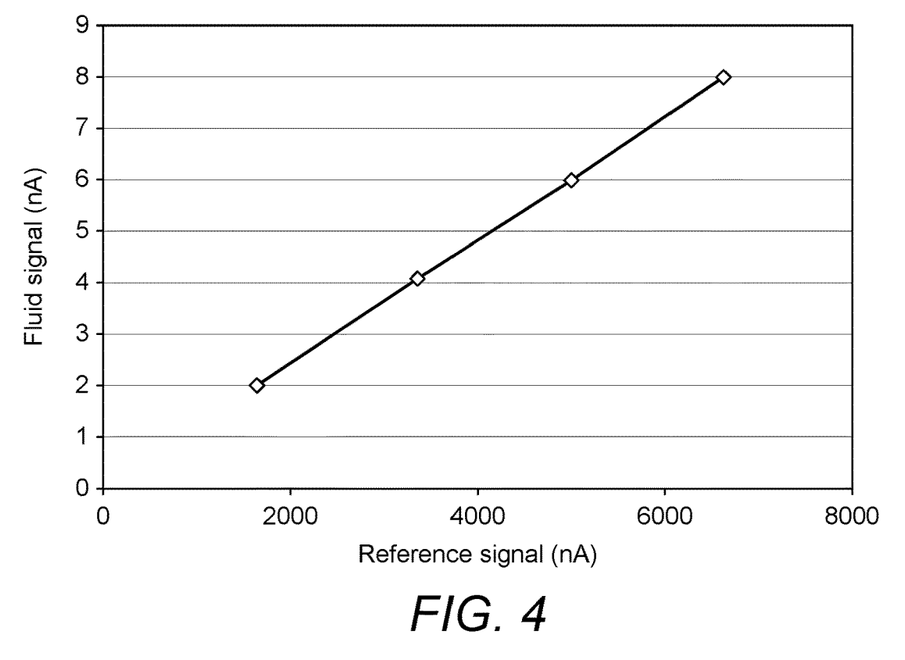
FIG. 4 shows a calibration graph for the turbidity sensor when using a 10 NTU calibration sample with four optical tests from 25% to 100% power.

FIG. 4 shows the results obtained by illuminating a 10 NTU control (i.e. calibration) sample with an LED (light emitting diode) emitting near-infrared light at a wavelength of around 860 nm and measuring the light detected at a photodiode (i.e. the second optical detector 30) positioned at a relative angle θ of 90° (i.e. the angle from the incident light). The fluid and reference signals were collected when running four optical tests (25%, 50%, 75% and 100% power of the emitter 10). The results are shown in ascending order or power and the current of the fluid and reference signals are shown in nA. A highly accurate regression line can be plotted between the plurality of points because the relationship is near linear. The slope of the regression line is then calculated to produce the calibration factor 216 using the following equation:

$$\text{Calibration Factor} = \text{Sample Turbidity/Gradient} \qquad \text{Equation (1)}$$

The calibration factor (or gain) based on the 10 NTU sample is 8333.33 (10 NTU/0.0012).

Figure 5:
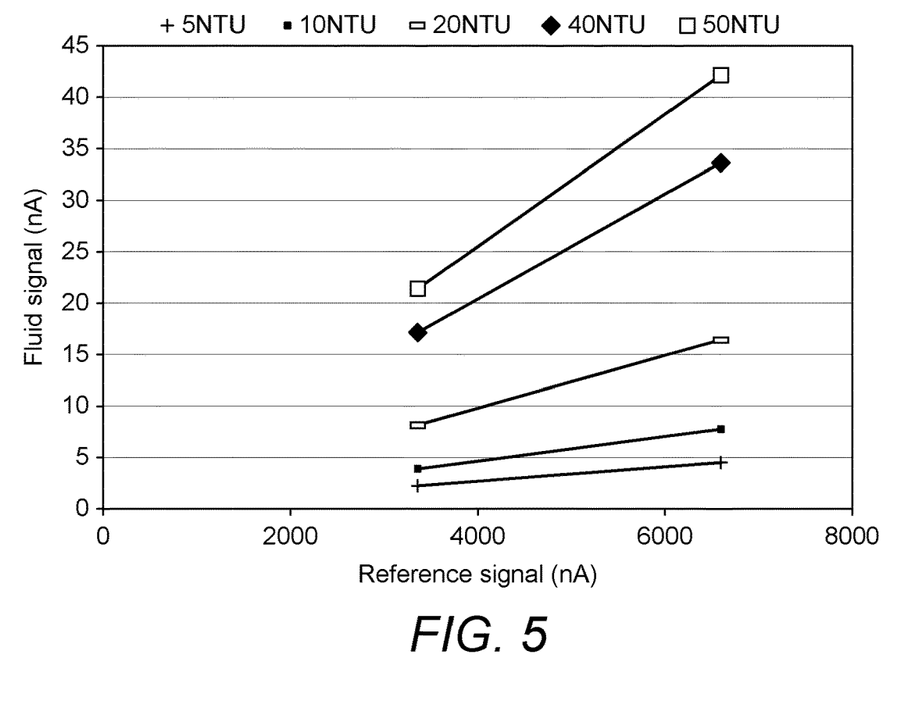
FIG. 5 shows calibration graphs for the turbidity sensor when using calibration samples having high turbidity (from 5 NTU to 50 NTU) each with two optical tests at 50% and 100% power.
Figure 6:
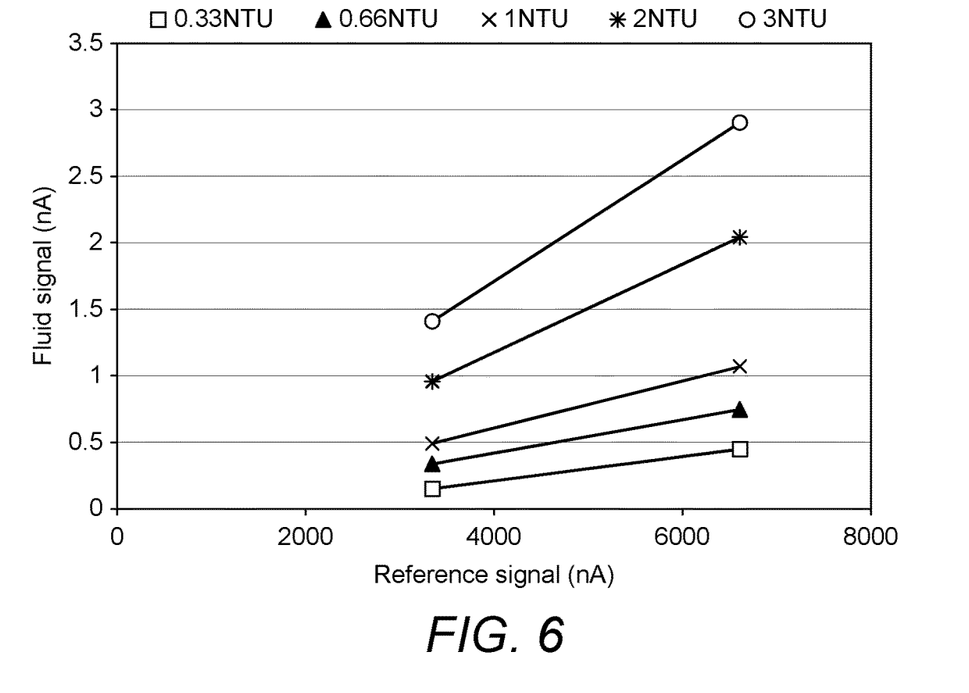
FIG. 6 shows calibration graphs for the turbidity sensor when using calibration samples having low turbidity (from 0.33 NTU to 3 NTU) each with two optical tests at 50% and 100% power.
Figure 7:
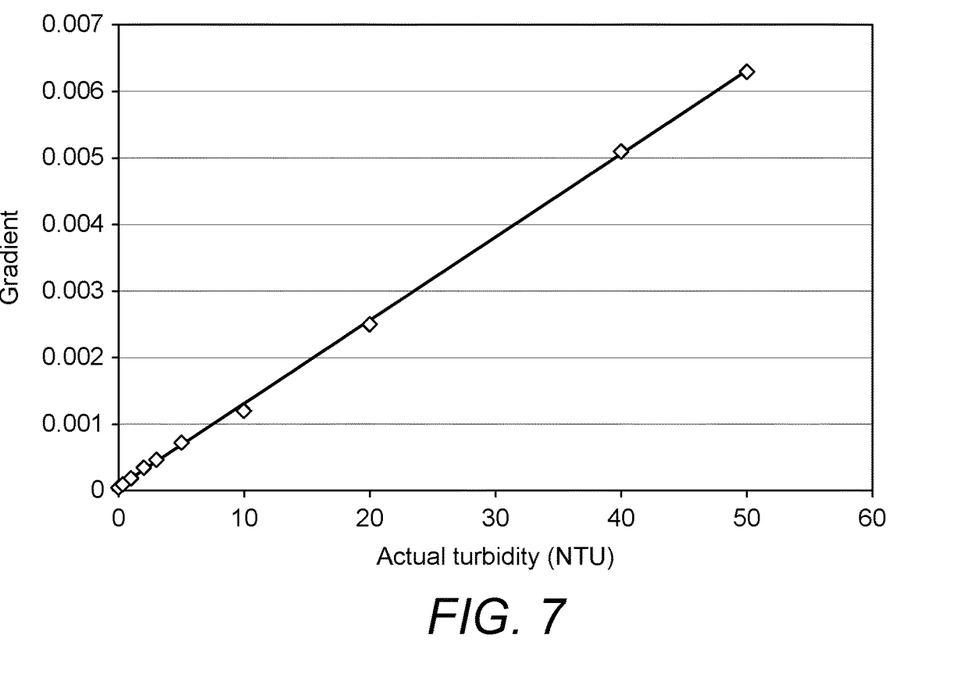
FIG. 7 shows the near-linear relationship between the gradient of the calibration lines of FIGS. 4 and 5 with the actual turbidity of the calibration samples.

The regression line of FIG. 4 would continue to intersect the y-axis at near zero. This relationship is shown when collecting samples from high and low level turbidity control samples as shown in FIGS. 5 and 6, respectively. In contrast to FIG. 4, each optical test 210 was run at only 50% and 100% power of the emitter 10. The regression lines plotted for each control sample show that the gradient changes with turbidity. In fact, the relationship is highly linear and the gradient appears to be directly proportional to turbidity, as shown in FIG. 7. Here, the gradients calculated from the high and low optical tests 210 are plotted against the turbidity of each control sample. The coefficient of determination ($R^2$) of the resulting regression line is 0.999.

As further shown in FIG. 3, the method 200 further includes repeating the optical test for a sample fluid 220 to calculate the turbidity of the sample fluid 226 using the calibration factor previously obtained 216 (as shown in the right-hand box with dashed lines). As with the control sample, the optical test begins with providing a sample fluid within which the turbidity sensor 100 is submersed. A plurality of optical signals are then sent into the sample fluid from the emitter 10 and each time a reference 223 and fluid signal 224 is captured. Once all the tests are run 225, the reference and fluid signals are plotted for each optical test and the gradient resulting from the regression line is calculated. A rearranged version of Equation (1) is then used to calculate the turbidity of the sample fluid:

$$\text{Sample Turbidity} = \text{Calibration Factor} \times \text{Gradient} \qquad \text{Equation (2)}$$

Figure 8:
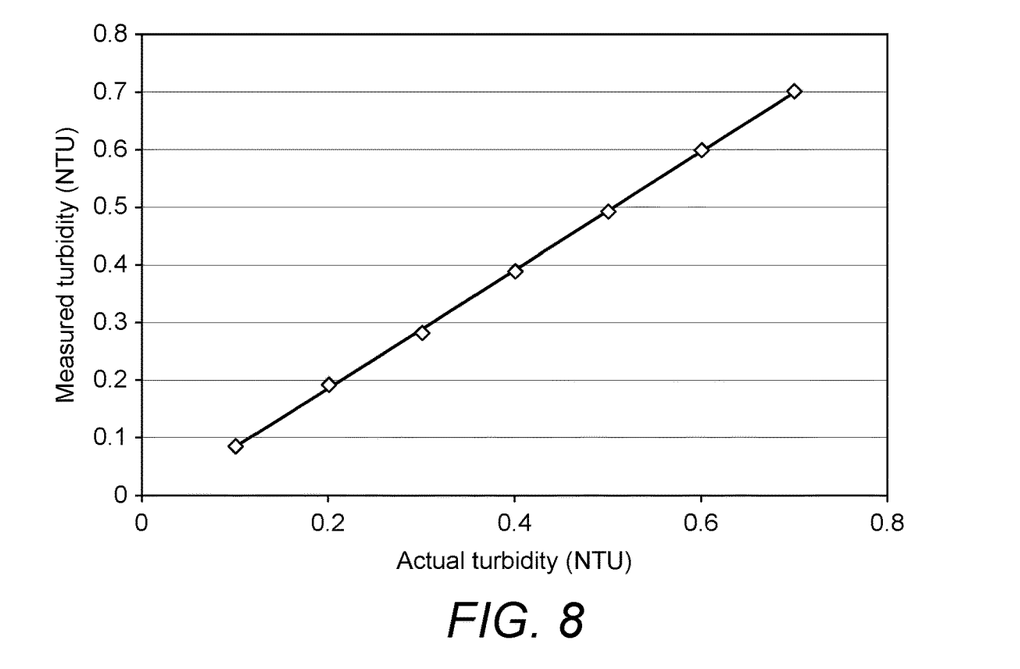
FIG. 8 shows a comparison between the low turbidity readings (from 0.1 NTU to 0.7 NTU) captured by the turbidity sensor with the actual turbidity of the calibration samples.
Figure 9:
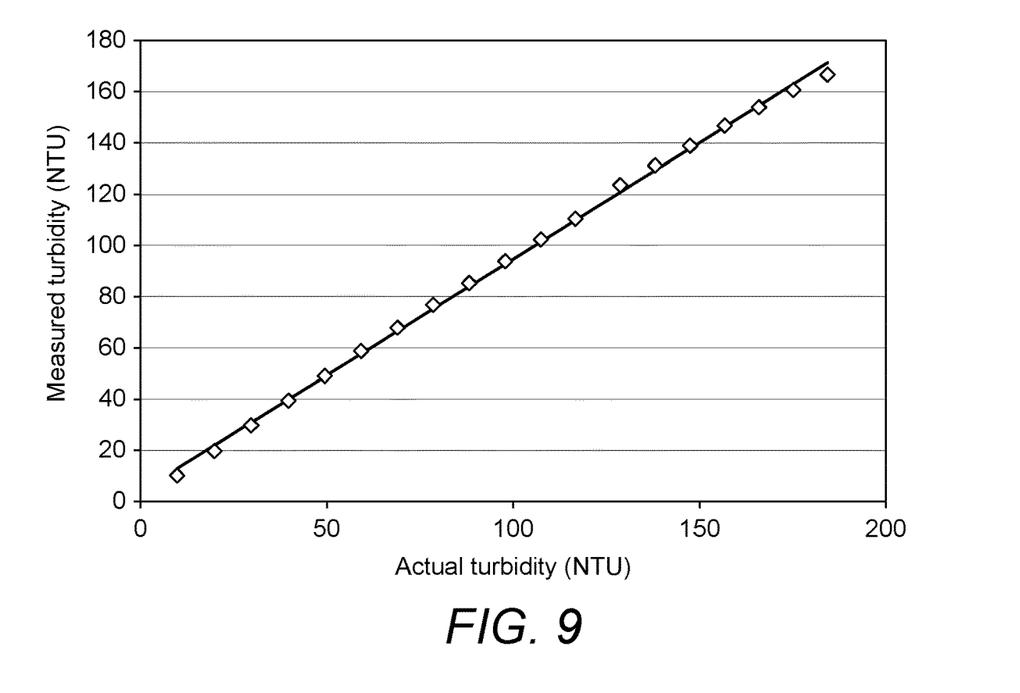
FIG. 9 shows a comparison between the high turbidity readings (from 10 NTU to 184 NTU) captured by the turbidity sensor with the actual turbidity of the calibration samples.

The results for measuring low and high levels of turbidity (0.1 to 184 NTU) with a turbidity sensor calibrated using a 10 NTU sample are shown in FIGS. 8 and 9, whereby a coefficient of determination ($R^2$) for each graph is at least 0.999.

The turbidity sensor 100 and method 200 uses an alternative approach of calculating turbidity. The method 200 allows for simple calibration and gives stable results. In summary, the method 200 involves taking measurements at different light levels in very close succession (the frequency of the optical tests with be at least 1 Hz, 5 hz or 10 Hz). This means that a calibration can be carried out using a single sample because varying the light output results in a relationship between turbidity and the detected signal. This avoids the influence of changes in background light levels. The gradient of a regression line plotted for the plurality of readings captured during the optical test by the first 20 and second 30 detectors is then used to determine the sample turbidity when a calibration factor is known. Since the optical tests are taken in rapid succession, the influence of the background is negligible because the background can be assumed to be stationary. This means that the gradient is not affected by the background and true readings of turbidity can be obtained.

Advantageously, an improved turbidity sensor 100 and method for measuring turbidity is provided. The improved turbidity sensor 100 and method produces accurate turbidity measurements across a wide range of samples. Beneficially, only a single calibration sample is needed to calibrate the turbidity sensor 100 because the background radiation can be ignored. Overall, a better optical sensor 100 and method for measuring turbidity is provided that solves the drawbacks associated with conventional turbidity sensors and methods.

Although preferred embodiment(s) of the present invention have been shown and described, it will be appreciated by those skilled in the art that changes may be made without departing from the scope of the invention as defined in the claims.

The invention claimed is:

1. A method of measuring turbidity with a nephelometric turbidity sensor, comprising:
   conducting an optical test on a control fluid with known turbidity to derive a calibration factor for the nephelometric turbidity sensor;
   emitting a plurality of optical signals in sequence from an emitter toward a sample fluid of unknown turbidity, each of the optical signals having a different intensity setting;
   capturing, for each of the optical signals, a reference signal value by detecting an intensity of the optical signal before entering the sample fluid, and a fluid signal value by detecting an intensity of the optical signal after entering the sample fluid; and,
   determining a turbidity measurement of the sample fluid by calculating a gradient of a regression line between plotted points of the reference and fluid signal values for each of the plurality of optical signals and multiplying the gradient of the regression line by the calibration factor.

2. The method of claim 1, wherein the plurality of optical signals comprise a primary optical signal and one or more non-primary optical signals having an intensity in the range of about 10% to 90% of the primary optical signal.

3. The method of claim 2, wherein the one or more non-primary optical signals have an intensity in the range of about 25% to 75% of the primary optical signal.

4. The method of claim 2, wherein the primary optical signal is created at substantially full power of the emitter.

5. The method of claim 1, wherein the plurality of optical signals are output with a frequency of at least 1 Hz, whereby the plurality of optical signals are output in succession within one second.

6. The method of claim 1, wherein the plurality of optical signals are output with a frequency of at least 5 Hz or at least 10 Hz.

7. The method of claim 1, wherein each of the optical signals in the plurality of optical signals has a duration of less than about 100 mS.

8. The method of claim 1, wherein each of the optical signals in the plurality of optical signals are separated in succession by a period of less than about 10 mS.

9. The method of claim 1, wherein the optical signals have a duration and separation which is sufficient to equalise background conditions while performing the turbidity measurement.

10. The method of claim 1, wherein the gradient of the regression line is directly proportional to the turbidity measurement.

11. The method of claim 1, wherein deriving the calibration factor comprises:
    emitting a plurality of optical signals in sequence from an emitter toward a control fluid of known turbidity, each of the optical signals having a different intensity setting;
    capturing, for each of the optical signals, a reference signal value by detecting an intensity of the optical signal before entering the control fluid, and a fluid signal value by detecting an intensity of the optical signal after entering the control fluid; and,
    calculating a gradient of a regression line between plotted points of the reference and fluid signal values for each of the plurality of optical signals and dividing the known turbidity of the control fluid by the gradient of the regression line to derive the calibration factor.

12. A nephelometric turbidity sensor, comprising:
    an emitter configured to emit optical signals toward a fluid;
    first and second optical detectors in a housing, wherein the first optical detector is arranged to receive the optical signal before entering the fluid and the second optical detector is arranged to receive the optical signal after entering the fluid; and,
    a controller configured to measure turbidity of a sample fluid of unknown turbidity by:
        storing a calibration factor derived from a control fluid of known turbidity;
        causing the emitter to output a plurality of optical signals in succession toward the sample fluid, each of the optical signals having a different intensity setting;
        capturing, for each of the optical signals, a reference signal value from the first optical detector before entering the sample fluid and a fluid signal value from the second optical detector after entering the sample fluid; and,
        determining a turbidity measurement of the sample fluid by calculating a gradient of a regression line between plotted points of the reference and fluid signal values for each of the plurality of optical signals and multiplying the gradient of the regression line by the calibration factor.

13. The nephelometric turbidity sensor of claim 12, further comprising a blocking member configured to block a direct line of incidence from the emitter to the second optical detector.

14. The nephelometric turbidity sensor of claim 13, wherein the blocking member is disposed between the first and second optical detectors.

15. The nephelometric turbidity sensor of claim 12, wherein the housing comprises a blocking member, the blocking member being configured as a step.

16. The nephelometric turbidity sensor of claim 12, wherein the second optical detector is arranged at substantially 90 degrees to a main line of incidence from the emitter.

17. The nephelometric turbidity sensor of claim 12, further comprising a collimating member configured to collimate the optical signal from the emitter.

18. The nephelometric turbidity sensor of claim 12, further comprising one or more sealing members configured to prevent the ingress of liquid beyond the emitter and the first and second optical detectors and into the housing when the sensor is submersed in the fluid.

* * * * *